United States Patent [19]

Bender, deceased et al.

[11] Patent Number: 4,539,315
[45] Date of Patent: * Sep. 3, 1985

[54] SUBLINGUALLY ABSORBABLE NONTOXIC ASPIRIN COMPOSITION

[75] Inventors: Charles E. Bender, deceased, late of Fairfield, Pa.; Audrey L. Bender, executrix, Huntington Valley, Pa.

[73] Assignee: Dynatech Laboratories, Incorporated, Alexandria, Va.

[*] Notice: The portion of the term of this patent subsequent to May 1, 2001 has been disclaimed.

[21] Appl. No.: 547,130

[22] Filed: Oct. 31, 1983

Related U.S. Application Data

[63] Continuation-in-part of Ser. No. 357,074, Apr. 11, 1982, Pat. No. 4,446,132.

[51] Int. Cl.³ .................... A61K 31/61; A61K 31/615
[52] U.S. Cl. .................... 514/162; 514/161; 514/960
[58] Field of Search ................. 424/233, 234

[56] References Cited

U.S. PATENT DOCUMENTS 2,101,867  12/1937  Miller et al. ............ 424/233
4,206,209  6/1980  Kracauer ............... 424/230

Primary Examiner—Stanley J. Friedman
Attorney, Agent, or Firm—LeBlanc, Nolan, Shur & Nies

[57] ABSTRACT

An analgesic aspirin composition in dosage form having acetylsalicylic acid and unreacted glycine in an amount equal to at least approximately 33.3% of the weight of the acetylsalicylic acid for rendering the aspirin nontoxic upon swallowing the aspirin composition, as well as rendering the aspirin sublingually absorbable.

9 Claims, No Drawings

SUBLINGUALLY ABSORBABLE NONTOXIC ASPIRIN COMPOSITION

This is a continuation-in-part of copending application Ser. No. 357,074 filed on April 11, 1982 for Nontoxic Aspirin Composition, now U.S. Pat. No. 4,446,132.

This invention relates to compositions containing analgesic acetylsalicylic acid (ASA).

Aspirin (acetylsalicylic acid) has been the most commonly used medication since its introduction many years ago. It has been regarded by the public as the thing nearest to a completely safe drug available on the market.

While aspirin taken occasionally in limited dosages is relatively safe, it has certain disadvantages. It has a bitter taste, so that it is generally taken in the form of tablets rather than in solution or as a powder. Moreover, when used regularly, it has undesirable side effects which limit its utility. Where massive dosages are needed, as in the case of chronic arthritis, these side effects—generally known as salicylate poisoning—often limit the dosages to a level at which they are no longer effective. In many cases, particularly where a patient has an underlying mild-to-moderate chronic atrophic gastritis, aspirin aggravates the condition to cause the gastritis to become hemorrhagic. This effect also seems to be due to the conversion of the aspirin to salicylic acid salts, and is related to the appearance of salicylates in the blood stream.

It has been proposed (U.S. Pat. No. 2,933,821) to combine aspirin with lysine in order to overcome its bitter taste, and produce an aspirin composition without the characteristic bitter taste of aspirin. However, this combination has no effect on the toxic side effects of aspirin—it still degrades to the salicylic acid in vivo, and the salicylates which appear in the blood stream have the same toxic effects as with unblended aspirin.

I have found that acetylsalicylic acid, when combined, but not reacted, with 33.3% to 222% of its weight of glycine, not only loses its bitter taste, but also is prevented from breaking down into salicylates in the stomach, so that the common toxic side effects of aspirin are overcome.

This invention is based on my discovery that glycine suppresses the in vivo breakdown of acetylsalicylic acid to salicylic acid and its salts if glycine is mixed with acetylsalicylic acid in an amount at least equal to approximately 33.3% of the weight of the acetylsalicylic acid that is present in the composition and preferably in an amount equal to approximately 55.6% of the weight of the acetylsalicylic acid. For an analgesic aspirin composition containing 90% by weight of acetylsalicylic acid and 10% by weight of starch, the amount of glycine used is equal to at least 30% of the weight of the aspirin composition and is preferably present in an amount equal to 50% of the aspirin composition. I may use more glycine without impairing the therapeutic effect of the asprin, but for cost reasons, I prefer not to use glycine in an amount in excess of approximately 200% of the weight of the 90% pure aspirin composition mentioned above. Mixing glycine with the acetylsalicylic acid in an amount at least approximately equal to 33.3% of the weight of the acetylsalicylic acid which is present in the composition is sufficient to substantially suppress in vivo breakdown of the acetylsalicylic acid into salicylic acid and its salts without impairing the therapeutic effect of acetylsalicylic acid.

In addition to the inert materials normally present in the aspirin tablets, I may add small amounts of taste-improving additives, such as, for example, mannitol, sugars, and various flavoring agents. The pH can be adjusted close to the neutral point to produce an aspirin tablet which can not only be swallowed whole but which can be sucked, chewed, or allowed to dissolve sublingually.

Extensive clinical testing of the medication over a period of time indicates that the medication of this invention is as effective as ordinary aspirin in relieving pain. A group of fifty patients, ranging in age from 5 to 76, was treated with tablets containing 325 milligrams (500 grains) of acetylsalicylic acid and having the following composition, based on total weight of the formulation:

Aspirin composition (containing 90% by weight of acetylsalicylic acid and 10% by weight of starch)—64.6%
Glycine (aminoacetic acid)—31.3%
Sodium saccharin—0.4%
Sodium cyclamate—3.6%
Lemon flavor (FLAVO-LOCK)—0.1%.

In general, young children preferred a sweeter-tasting product; pain was relieved in most cases, but not in all, as in a similar group of control patients treated with ordinary aspirin. Significantly, of the group treated with my medication there were five patients with records of gastritis, or stomach or intestinal ulcers, all of whom suffered upset stomachs or bleeding under aspirin therapy. None of them reported any such symptoms when treated with the above composition.

In place of sodium saccharin, a like amount of sodium cyclamate may be used in the above composition, making the total amount of sodium cyclamate present equal to 4.0% of the total weight of the composition. Alternatively, the sodium cyclamate may be replaced with a like amount of sodium saccharin in the above composition, making the total amount of sodium saccharin present equal to 4.0% of the total weight of the composition.

From the description thus far it will be appreciated that the foregoing composition is an admixture of the acetylsalicylic acid, the glycine and the other ingredients stated above. The glycine is therefore unreacted with the acetylsalicylic acid prior to administering the composition in suitable unit dosage form such as tablets. Rather than being added to water or some other reaction medium, the glycine/ASA mixture of this invention is therefore added to the acidic stomach fluids where the unreacted glycine has the effect of suppressing the in vivo breakdown of the acetylsalicylic acid into its salts. The present invention therefore contemplates the activity by the unreacted glycine to suppress the usual toxic effects of acetylsalicylic acid.

Observation in additional clinical tests indicate that because of the presence of unreacted glycine the foregoing composition will react sufficiently with the saliva in the human mouth to pass the medication sublingually into the blood stream to establish the presence of salicylates in the blood. The sublingual absorption may be achieved by sucking or chewing on tablets of the foregoing composition and was observed to provide more rapid and more effective relief than pure aspirin. Additionally, it has been observed that the presence of the unreacted glycine in the composition causes the acetylsalicylic acid to lose its bitter taste, thus permitting sublingual absorption without the objectionable taste of pure aspirin. For sublingual absorption, the tablet form of the foregoing composition is orally administered in tablet form without the addition of water. The pH of the composition of this invention in tablet form is mildly acidic and greater than 4.

The following admixture (in which the percentages are based on total weight of the formulation) is also effective to suppress in vivo breakdown of the acetylsalicylic acid in the human stomach and to provide for sublingual absorption of the medication:

Aspirin composition (containing 90% by weight of acetylsalicylic acid and 10% by weight of starch)—61.6%
Glycine—30.2%
Sodium saccharin—0.4%
Sodium cyclamate—3.4%
Peppermint flavor—0.4%
Corn starch—2.0%
Gelatin powder (100 bloom)—2.0%.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of sublingually treating headaches and other disorders normally treated with aspirin comprising the steps of providing an admixture comprising acetylsalicylic acid and glycine in dosage form in which the glycine is unreacted with said acid, and placing the dosage form of said admixture in the human mouth without swallowing it for reaction with the saliva in the mouth, the unreacted glycine in said admixture being present in an amount effective to cause the acetylsalicylic acid to react sufficiently with the saliva to sublingually pass the medication in said admixture into the blood stream.

2. The method defined in claim 1 wherein the amount of glycine present in said admixture is equal to at least one-third of the weight of the acetylsalicylic acid.

3. The method defined in claim 1 wherein the amount of glycine present in said admixture is equal to approximately 55% of the weight of the acetylsalicylic acid in the admixture.

4. The method defined in claim 1 wherein the dosage form of said admixture is a tablet form.

5. The method defined in claim 4 wherein said admixture includes a quantity of starch mixed with the glycine and the acetylsalicylic acid.

6. A method of producing an aspirin medication for treating headaches and other disorders normally treated with aspirin, comprising the steps of providing a liquid-free admixture comprising glycine and acetylsalicylic acid in which said glycine is unreacted with said acid, and forming tablets in dosage form ready to be swallowed whole or dissolved in the mouth so that the glycine is still unreacted with said acid upon orally administering the tablets, the unreacted glycine in said admixture being present in an amount sufficient to cause the acetylsalicylic acid to react sufficiently with the saliva in the human mouth to sublinqually pass the medication into the blood stream, and said amount of said glycine also being sufficient to suppress the in vivo breakdown of said acetylsalicylic acid to salicylic acid and its salts in the human stomach, all without substantially impairing the therapeutic effect of said acetylsalicylic acid.

7. The method defined in claim 6 wherein the amount of glycine present in said admixture is equal to at least $\frac{1}{3}$ of the weight of the acetylsalicylic acid.

8. The method defined in claim 6 wherein the amount of glycine present in said admixture is equal to approximately 55% of the weight of the acetysalicylic acid in the mixture.

9. The method defined in claim 6 wherein said admixture includes a quantity of starch mixed with the glycine and acetysalicylic acid.

* * * * *